United States Patent [19]

Hajos et al.

[11] 4,237,055

[45] Dec. 2, 1980

[54] SYNTHESIS OF 1RS,4SR,5RS-4-(4,8-DIMETHYL-5-HYDROXY-7-NONEN-1-YL)-4-METHYL-3,8-DIOXABICYCLO[3.2.1]OCTANE-1-ACETIC ACID

[75] Inventors: Zoltan G. Hajos, Princeton; Michael P. Wachter, Bloomsbury, both of N.J.

[73] Assignee: Ortho Pharmaceutical Corporation, Raritan, N.J.

[21] Appl. No.: 49,760

[22] Filed: Jun. 18, 1979

[51] Int. Cl.$^3$ ............................................. C07D 319/00
[52] U.S. Cl. ........................ 260/340.6; 260/340.9 R; 260/347.8; 260/348.25; 556/436; 556/482; 560/60; 568/662; 568/663; 568/308;

[58] Field of Search ............................ 260/340.6, 347.8

[56] References Cited

U.S. PATENT DOCUMENTS 4,102,895 7/1978 Kanojia et al. .................. 260/340.6

OTHER PUBLICATIONS

Cram & Hammond, Organic Chemistry, p. 355.

*Primary Examiner*—Ethel G. Love
*Attorney, Agent, or Firm*—Benjamin F. Lambert

[57] ABSTRACT

A method of synthesizing 1RS,4SR,5RS-4-(4,8-dimethyl-5-hydroxy-7-nonen-1-yl)-4-methyl-3,8-dioxabicyclo [3.2.1]octane-1-acetic acid. The acid is a derivative of the natural product zoapatanol, one of the active ingredients in the zoapatle plant, and is active as a uteroevacuant agent.

14 Claims, No Drawings

1

SYNTHESIS OF 1RS,4SR,5RS-4-(4,8-DIMETHYL-5-HYDROXY-7-NONEN-1-YL)-4-METHYL-3,8-DIOXABICYCLO[3.2.1]OCTANE-1-ACETIC ACID

The isolation and structural determination of zoapatanol, 2S,3R,6E-(2''-hydroxyethylidene)-2-methyl-2-(4',8'-dimethyl-5'-oxo-7'-nonenyl)-oxepan-3-ol, one of the active ingredients in the zoapatle plant, is described in U.S. Pat. No. 4,086,358. In U.S. Pat. No. 4,102,895, a synthesis for 1RS,4SR,5RS-4-(4,8-dimethyl-5-hydroxy-7-nonen-1-yl)-4-methyl-3,8-dioxabicyclo[3.2.1] octane-1-acetic acid, a derivative of zoapatanol, is described. The bicyclic derivative has the following formula:

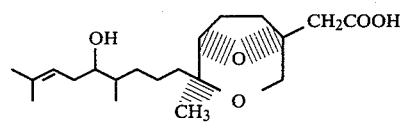

The present invention relates to a method of synthesizing 1RS,4SR,5RS-4-(4,8-dimethyl-5-hydroxy-7-nonen-1-yl)-4-methyl-3,8-dioxabicyclo[3.2.1]octane-1-acetic acid. The acetic acid derivative is active as a uteroevacuant agent. Many of the intermediates employed in the synthesis are novel compounds and are included as part of the invention.

The synthesis is comprised of several steps which are summarized in the following schematic diagram:

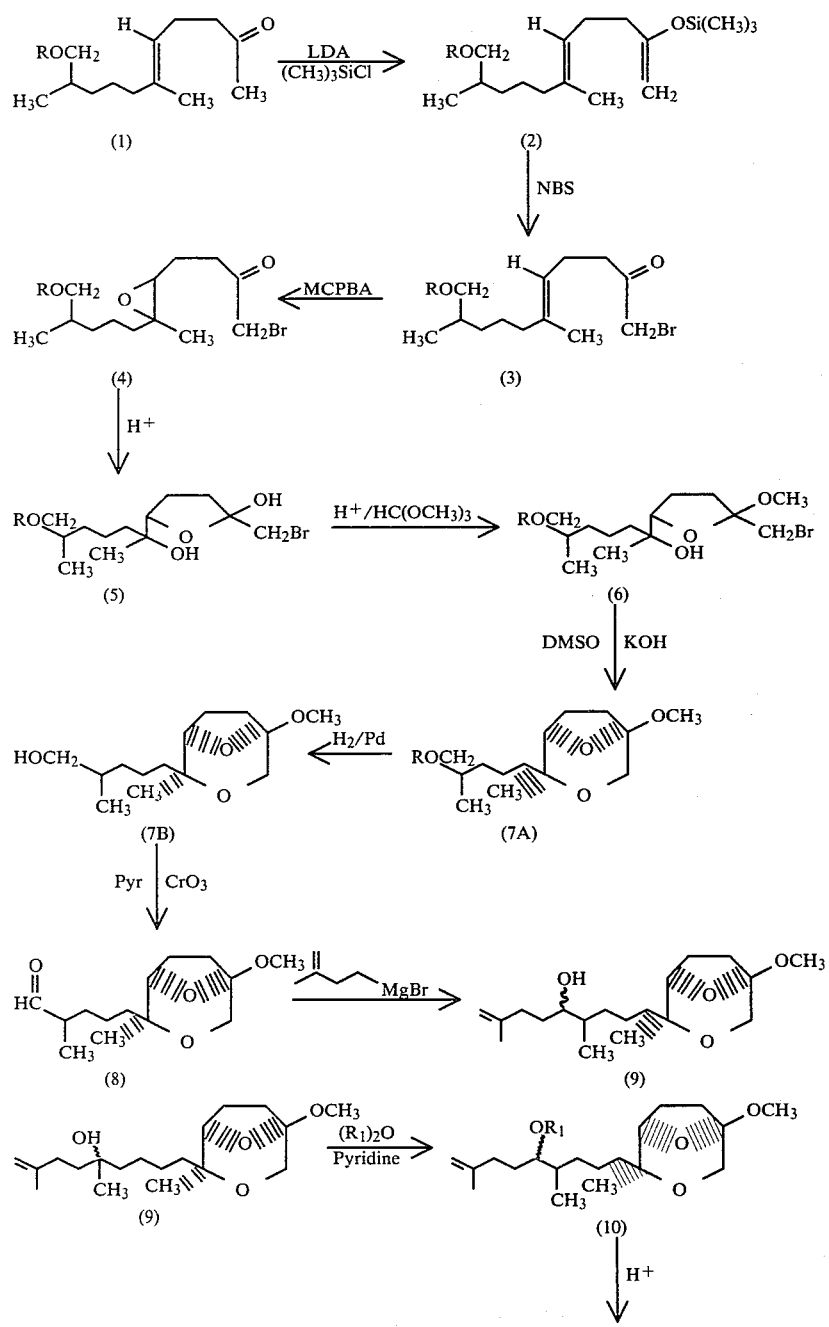

-continued

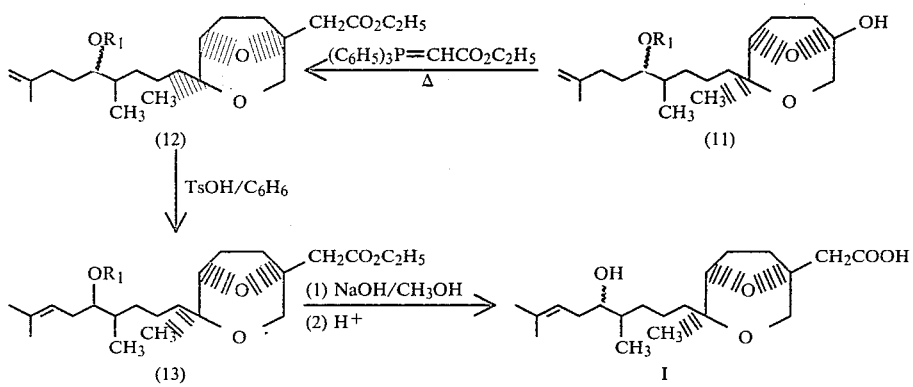

wherein R is benzyl or Si($C_6H_5$)$_2tC_4H_9$; $R_1$ is lower alkanoyl having 2-5 carbon atoms; TsOH is p-toluenesulfonic acid; LDA is lithium diisopropylamide; NBS is N-bromosuccinimide; and CPBA is m-chloroperbenzoic acid.

The conversion of the unsaturated ketone (1), either as a mixture of E:Z isomers or as the pure E isomer to the bicyclic oxido-oxepane intermediates, 7A and 7B, is carried out as shown in the schematic diagram above. The synthetic method is identical for both analogs and is described only for the conversion of the analog having the benzyl group.

The first step in the synthesis involves the conversion of the unsaturated ketone 1-benzyloxy-2,6-dimethyl-10-oxo-undec-6-ene (1) to the silyl enol ether (2) by reaction first with lithium diisopropylamide followed by reaction with trimethylsilyl chloride in the presence of a base such as triethylamine or pyridine. A mild base such as an alkali metal bicarbonate such as sodium bicarbonate followed by aqueous sodium bicarbonate is added to the reaction mixture and the silyl enol ether (2) is isolated from the mixture by techniques known to those skilled in the art. The reaction is carried out at a temperature between −80° C. and +20° C. The preferred temperature is about −70° C. Solvents which can be employed include tetrahydrofuran, dimethoxyethane and dioxane.

The silyl enol ether (2) is then brominated with a brominating agent such as bromine or N-bromosuccinimide, for example, in the presence of a mild alkali such as sodium bicarbonate, for example, to give a bromoketone (3). The reaction is carried out at a temperature between −80° C. and −20° C. The preferred temperature is −70° C. Suitable solvents which can be employed include tetrahydrofuran, dimethoxyethane and dioxane.

The bromo-ketone (3) is then epoxidized with a peracid such as m-chloroperbenzoic acid, monoperphthalic acid, peracetic acid or trifluoroperacetic acid to give the corresponding epoxide (4). The reaction is carried out at a temperature between −10° C. and +10° C. The preferred temperature is 0° C. As the solvent for the reaction, solvents such as methylene chloride, chloroform, ether and dichloroethane may be employed. Upon treatment with acid, the epoxide is converted to a 5-membered ring hemiketal (5). Dilute acids, such as hydrochloric acid and sulfuric acid, can be employed and suitable solvents for the reaction include acetone, butanol and tetrahydrofuran.

The hemiketal (5) is then protected for subsequent steps by treating it with an alcoholic alkylating agent such as methanol, ethanol, propanol, butanol and the like in the presence of an anhydrous acid such as, for example, anhydrous hydrochloric acid, sulfuric acid and phosphoric acid, a trialkylorthoformate such as trimethyl, triethykl, tripropyl and tributylorthoformate and the like or N,N-dimethylformamide dimethyl acetal, for example, in a weakly acidic solution to form a bromohydroxy acetal (6). Where an excess of the reagent is employed it can also serve as the solvent. Acids which can be employed include dilute sulfuric acid, hydrochloric acid and phosphoric acid. Suitable solvents include methanol and tetrahydrofuran. The reaction is generally carried out at a temperature between −5° C. and +20° C. The preferred temperature range is 0° C. to 5° C.

Cyclization of the bromohydroxy acetal (6) with an alkali metal hydroxide or alkoxide such as potassium hydroxide, sodium hydroxide, potassium tertiary butoxide or a metal hydride such as sodium hydride in a suitable solvent such as dimethylsulfoxide, dimethylformamide or tetrahydrofuranhexamethylphosphoramide gives the bicyclic oxido-oxepane (7A). The reaction is carried out at a temperature between 20° C. and 80° C. The preferred temperature range is 55° C. to 65° C. When the ketone having the t-butyldiphenylsilyl protecting group on the side chain is employed as the starting material, the bicyclic alcohol (7B) is obtained directly in the cyclization step with simultaneous loss of the t-butyldiphenylsilyl protecting group. However, when cyclization is carried out with the alcohol (6) having a benzyl group as the protecting group the benzyl protected oxido-oxepane (7A) is obtaind in the cyclization step. Hydrogenolysis of the benzyl protected oxido-oxepane with hydrogen in the presence of a catalyst such as palladium, for example, gives the free alcohol (7B).

Oxidation of the alcohol (7B) with a suitable oxidizing agent such as, for example, chromium trioxide in pyridine, chromium trioxide in dimethylformamide and pyridinium chlorochromate gives the corresponding bicyclic aldehyde (8). Reaction of the aldehyde with 3-methyl-3-butenyl magnesium bromide gives a secondary alcohol (9) having the requisite number of carbon atoms in the long side chain at $C_2$. The reaction is preferably carried out at a temperature between −20° C. and 25° C. in a suitable solvent such as tetrahydrofuran or dioxane. The alcohol (9) is protected by converting it to an ester (10) by reaction with a lower alkanoic acid anhydride such as acetic anhydride, propionic anhydride or butyric anhydride in the presence of a base such as pyridine, sodium acetate or triethylamine.

The ketal protecting group is then hydrolyzed with dilute acid such as hydrochloric acid, sulfuric acid or acetic acid in a suitable solvent such as acetone or tetrahydrofuran to give a hemiketal (11). The reaction is preferably carried out at a temperature between room temperature and about 60° C. The functionalized side chain at $C_6$ is introduced by means of a Wittig reaction with (carbethoxy-methylene)-triphenylphosphorane to give a bicyclic ester (12). The reaction is carried out at a temperature between 90° C. and 140° C. It is preferred to carry out the reaction neat at a temperature of about 120° C. The terminal olefin in the bicyclic ester (12) is isomerized to a more stable olefin (13) with p-toluenesulfonic acid in a suitable solvent such as benzene, toluene or xylene at a temperature between 78° C. and 140° C. It is preferred, however, to carry out the reaction at a temperature of about 80° C. Hydrolysis of the diester (13) with an alcoholic base gives 1RS,4SR,5RS, -4-(4,8-dimethyl-5-hydroxy-7-nonen-1-yl)-4-methyl-3,8-dioxabicyclo[3.2.1]octane-1-acetic acid (I). Suitable alcoholic basic solutions which can be employed include methanol-sodium hydroxide-water, methanol-tetrahydrofuran-sodium hydroxide-water, methanol-dioxane-sodium hydroxide-water, methanol-dioxane-potassium hydroxide-water, methanol-dioxane-lithium hydroxide-water, methanol-dioxane-cesium hydroxide-water.

Chromatography of the bromohydroxy acetal (6), which contains a mixture of erythro and threo isomers, obtained from (1) as an E/Z mixture, results in a separation of the isomers. Starting with the unsaturated ketone (1) as the E isomer leads to a bromohydroxy acetal (6) as the pure erythro isomer. The erythro isomer gives the desired 1RS,4SR,5RS epimer of the oxido-oxepane (7A,7B), while the threo epimer gives the 1RS,4RS 5RS epimer. Thus, when the unsaturated ketone (1) having a benzyl protecting group is used as the starting material in the synthesis of the dioxabicyclic compound (I), the bicyclic oxido-oxepanes (7A and 7B) are obtaind as the pure 1RS,4SR,5RS epimers.

The unsaturated ketone (1) is synthesized from 1-benzyloxy-2-methyl-6-oxo-heptane or 1-t-butyldiphenylsiloxy-2-methyl-6-oxo-heptane depending upon whether R is a benzyl group or a t-butyldiphenylsilyl group. The benzyl protected compound is prepared from 6,6-ethylene-dioxy-2-methyl-heptanol by benzylation with a benzyl halide, such as benzyl bromide, followed by hydrolysis of the ketal to the corresponding ketone with dilute acid.

The synthesis of the unsaturated ketones (1) is carried out by several routes as illustrated below:

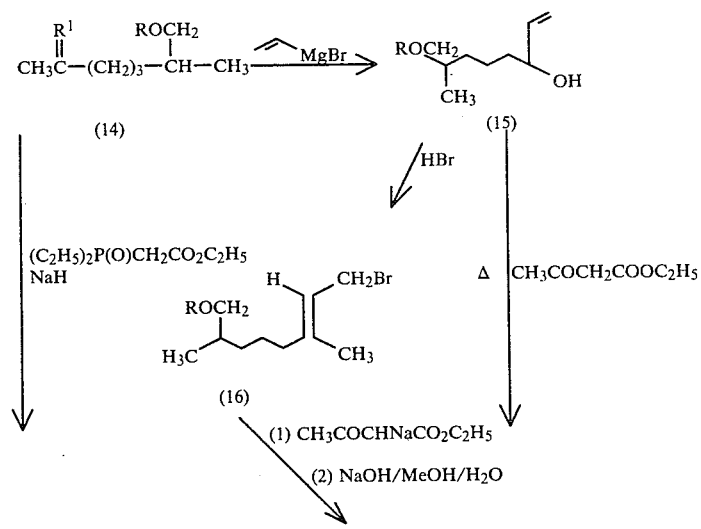

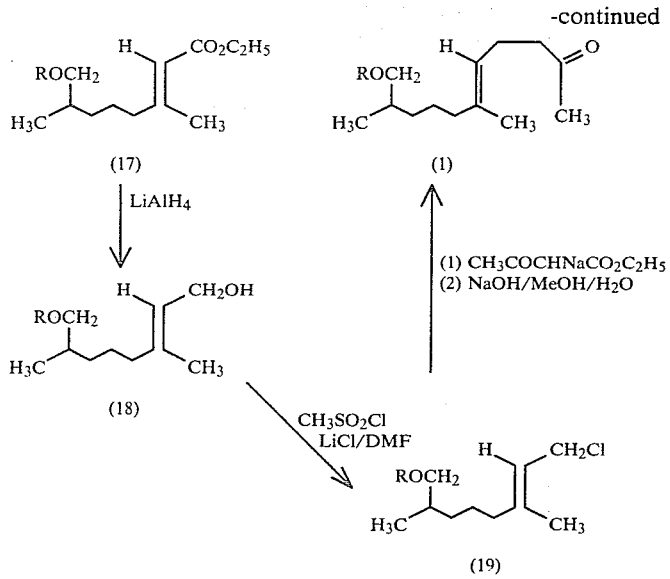

wherein R is a benzyl group, a t-butyldiphenylsilyl group or hydrogen and $R^1$ is oxo or

The Grignard reaction with vinyl magnesium bromide on the ketone (14, $R^1$=oxo) gives the vinyl carbinol (15) which is treated with ethylacetoacetate at 180° C. to give the unsaturated ketone (1) as E:Z isomers.

In another procedure, the allylic bromides (16) are synthesized by addition of an ethereal solution of anhydrous hydrobromic acid to the vinyl carbinol (15) which is then converted without isolation to the unsaturated ketone (1) by condensation with the sodio salt of ethylacetoacetate followed by hydrolysis and decarboxylation of the intermediate β-keto ester in methanolic base giving the unsaturated ketone (1) as E:Z isomers.

In a third method, the ketone wherein R is a benzyl group is synthesized as the pure E isomer by treating the ketone (14), wherein R is a benzyl group and $R^1$=oxo, with triethylphosphonoacetate to give an intermediate α,β-unsaturated ester (17) as a mixture of E:Z isomers. Reduction of the unsaturated ester (17) with lithium aluminum hydride gives a mixture of epimeric alcohols (18) from which the E isomer is isolated by chromatography. Conversion of the alcohol (18) to the allylic chloride (19) is carried out by reaction with methane-sulfonyl chloride, lithium chloride and dimethylformamide. The chloride (18) is then treated with sodioethylacetoacetate to give the unsaturated ketone (1) as the pure E isomer after hydrolysis and decarboxylation.

The following examples describe the invention in greater particularity and are intended to be a way of illustrating but not limiting the invention:

EXAMPLE 1

11-Benzyloxy-6,10-dimethyl-2-trimethylsiloxy-undec-1,5-diene

Lithium diisopropylamide was prepared by the addition of 2.1 M n-butyllithium in hexane (22.7 ml, 48.8 mM) to diisopropylamine (3.45 ml, 48.8 mM) in dry tetrahydrofuran (125 ml). The base is cooled to −70° C., 1-benzyloxy-2,6-dimethyl-10-oxo-undec-6-ene (12.4 g, 41 mM) in dry tetrahydrofuran (300 ml) is added and the mixture is allowed to stir for 1 hour. Trimethylsilyl chloride (14 ml, 111 mM) is added to triethylamine (3.7 ml, 26.8 mM) in dry tetrahydrofuran (50 ml). The mixture is centrifuged, and the supernatant is added to the lithio salt at −70° C. After 4 hours, sodium bicarbonate (2.5 g) and saturated sodium bicarbonate (250 ml) are added, the reaction mixture is partitioned between ether and brine, the aqueous phase is extracted with ether and the combined extracts are washed with brine and dried ($Na_2SO_4$). The solvent is removed in vacuo to give crude 11-benzyloxy-6,10-dimethyl-2-trimethylsiloxy-undec-1,5-diene.

EXAMPLE 2

11-t-Butyldiphenylsiloxy-6,10-dimethyl-2-trimethylsiloxy-undec-1,5-diene

Following the procedure for the preparation of 11-benzyloxy-6,10-dimethyl-2-trimethylsiloxy-undec-1,5-diene, but employing 6 E/Z-1-t-butyldiphenyl-siloxy-2,6-dimethyl-10-oxo-undec-6-ene (38 g) in place of 6 E/Z-1-benzylozy-2,6-dimethyl-10-oxo-undec-6-ene, 11-t-butyldiphenylsiloxy-6,10-dimethyl-2-trimethylsiloxy-undec-1,5-diene (44 g) is obtained as a yellow oil: nmr ($CDCl_3$)δ 0.92 (d, $CH_3CH$), 1.05 (s, $(CH_3)_3C$—), 3.45 (d, —$OCH_2CH$—), 4.01 (s, $CH_2$=C—), 5.06 (m, C=$CH$).

EXAMPLE 3

11-Benzyloxy-1-bromo-6,10-dimethyl-2-oxo-undec-5-ene

11-Benzyloxy-6,10-dimethyl-2-trimethylsiloxy-undec-1,5-diene (15.36 g, 41 mM) in dry tetrahydrofuran (400 ml) is treated with sodium bicarbonate (4.1 g, 49 mM) and N-bromosuccinimide (7.3 g, 41 mM) at −70° C. and allowed to stir for 4 hours. The reaction mixture is allowed to reach room temperature after which saturated sodium bicarbonate, ether and brine are added. The phases are separated, the aqueous phase is extracted with ether and the combined organic extracts are washed with brine and dried ($Na_2SO_4$). The solvent is removed in vacuo to give crude 11-benzyloxy-1-bromo-6,10-dimethyl-2-oxo-undec-5-ene (17 g).

EXAMPLE 4

11-t-Butyldiphenylsiloxy-1-bromo-6,10-dimethyl-2-oxo-undec-5-ene

Following the procedure for the preparation of 11-benzyloxy-1-bromo-6,10-dimethyl-2-oxo-undec-5-ene, but employing 11-t-butyldiphenylsiloxy-6,10-dimethyl-2-trimethylsiloxy-undec-1,5-diene (44.5 g) in place of 11-benzyloxy-6,10-dimethyl-2-trimethylsiloxy-undec-1,5-diene, 11-t-butyldiphenylsiloxy-1-bromo-6,10-dimethyl-2-oxo-undec-5-ene (45.8 g) is obtained as a yellow oil. Chromatography of a portion of the oil on silica using ethyl acetate-hexane gradients gives the pure product:

nmr (CDCl$_3$)δ 0.92 (d, CH$_3$CH), 1.05 (s, CCH$_3$)$_3$C—), 3.44 (d, —OCH$_2$CH), 3.83 (s, —COCH$_2$Br), 5.06 (m, C=CH), 7.2–7.8 (m, aromatic H).

EXAMPLE 5

11-Benzyloxy-1-bromo-6,10-dimethyl-5,6-epoxy-undecan-2-one

11-Benzyloxy-1-bromo-6,10-dimethyl-2-oxo-undec-5-ene (15.6 g, 41 mM) in methylene chloride (250 ml) is treated with 85% m-chloroperbenzoic acid (8.35 g, 41 mM) in methylene chloride (200 ml) at 0° C. for 3 hours. The reaction mixture is washed with brine, saturated sodium sulfite, brine and then dried (Na$_2$SO$_4$). The solvent is removed in vacuo to give crude 11-benzyloxy-1-bromo-6,10-dimethyl-5,6-epoxy-undecan-2-one (17.5 g).

EXAMPLE 6

11-t-Butyldiphenylsiloxy-1-bromo-6,10-dimethyl-5,6-epoxy-undecan-2-one

Following the procedure for the preparaton of 11-benzyloxy-1-bromo-6,10-dimethyl-5,6-epoxy-undecan-2-one, but employing 11-t-butyldiphenylsiloxy-1-bromo-6,10 -dimethyl-2-oxo-undec-5-ene (1.6 g) in place of 11-benzyloxy-1-bromo-6,10-dimethyl-2-oxo-undec-5-one, 11-t-butyldiphenylsiloxy-1-bromo-6,10-dimethyl-5,6-epoxy-undecan-2-one (1.3 g) is obtained as a yellow oil:

nmr (CDCl$_3$)δ 0.91 (d, CH$_3$CH), 1.05 (s, (CH$_3$)$_3$C—), 2.75 (overlapping t,

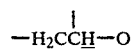

and —CH$_2$CO—), 3.45 (d, O—CH$_2$CH), 3.50 (s, —COCH$_2$Br), 7.2–7.8 (m, aromatic H); ms, m/e 487 (M-t-butyl).

EXAMPLE 7

7-Benzyloxy-2-(2-bromomethyl-2-hydroxy-tetrahydrofuran-5-yl)6-methyl-heptan-2-ol 11-Benzyloxy-1-bromo-6,10-dimethyl-5,6-epoxy-undecan-2-one (16.2 g, 41 mM) in acetone (170.5 ml) is treated with 0.2 N hydrochloric acid (18.75 ml) at 0° C. for 0.75 hours. The reaction mixture is then stirred at room temperature for 18 hours. The solvent is removed in vacuo and the residue obtained is treated with ether, brine and saturated sodium bicarbonate. The phases are separated and the aqueous phase is extracted with ether. The combined extracts are washed with brine and dried (Na$_2$SO$_4$). The solvent is removed in vacuo to give crude 7-benzyloxy-2-(2-bromomethyl-2-hydroxy-tetrahydrofuran-5-yl)-6-methyl-heptan-2-ol (17 g).

EXAMPLE 8

7-t-Butyldiphenylsiloxy-2-[2-bromomethyl-2-hydroxy-tetrahydrofuran-5-yl]-6-methyl-heptan-2-ol Following the procedure for the preparation of 7-benzyloxy-2-(2-bromomethyl-2-hydroxy-tetrahydrofuran-5-yl)-6-methyl-heptan-2-ol, but employing 11-t-butyldiphenyl-siloxy-1-bromo-6,10-dimethyl-5,6-epoxy-undecan-2-one (1.46 g) in place of 11-benzyloxy-1-bromo-6,10-dimethyl-5,6-epoxy-undecan-2-one, 7-t-butyldiphenylsiloxy-2-[2-bromo-methyl-2-hydroxy-tetrahydrofuran-5-yl]-6-methyl-heptan-2-ol (1.34 g) is obtained as a mixture of cis: trans isomers:

nmr (CDCl$_3$)δ 0.93 (d, CH$_3$CH), 1.05 (s, (CH$_3$)$_3$C—), 3.2–3.7 (overlapping m), 7.2–7.8 (m, aromatic H).

EXAMPLE 9

7-Benzyloxy-2-[2-bromomethyl-2-methoxy-tetrahydrofuran-5-yl]-6-methyl-heptan-2-ol 7-Benzyloxy-2-(2-bromomethyl-2-hydroxy-tetrahydrofuran-5-yl)-6-methyl-heptan-2-ol (16.9 g, 41 mM) is treated with distilled trimethylorthoformate (51 ml, 66 mM) and 0.1 N sulfuric acid/methanol (15.3 ml) at 0° C. for 0.5 hours and then at 5° C. for 66 hours. The solvent is removed in vacuo and the residue obtained is treated with ether, saturated sodium bicarbonate and brine. The layers are separated, the aqueous phase is extracted with ether and the combined ether extracts are washed with brine and dried (Na$_2$SO$_4$). The solvent is removed in vacuo to give crude 7-benzyloxy-2-[2-bromomethyl-2-methoxy-tetrahydrofuran-5-yl]-6-methyl-heptan-2-ol.

EXAMPLE 10

7-t-Butyldiphenylsiloxy-2-[2-bromomethyl-2-methoxy-tetrahydrofuran-5-yl]-6-methyl-heptan-2-ol 7-t-Butyldiphenylsiloxy-2-[2-bromomethyl-2-methoxy-tetrahydrofuran-5-yl]-6-methyl-heptan-2-ol is prepared as a mixture of cis:trans isomers by employing 7-t-butyldiphenylsiloxy-2-[2-bromomethyl-2-hydroxy-tetrahydrofuran-5-yl]-6-methyl-heptan-2-ol (1.33 g) in place of 7-benzyloxy-2-(2-bromomethyl-2-hydroxy-tetrahydrofuran-5-yl)-6-methyl-heptan-2-ol in the process for the preparation of 7-benzyloxy-2-[2-bromomethyl-2-methoxy-tetrahydrofuran-5-yl]-6-methyl-heptan-2-ol. The mixture of cis and trans isomers is separated by chromatography on silica gel (ethyl acetate:hexane gradient) to give the cis isomer as a yellow oil (0.324 g) and then the trans isomer as a yellow oil (0.151 g):

nmr cis-isomer (CDCl$_3$)δ 0.94 (d, CH$_3$CH), 1.06 [s, (CH$_3$)$_3$ C–], 3.22 and 3.24 (OCH$_3$), 3.5 (s, CH$_2$Br); ms, m/e 407 (m-t-Bu, H$_2$O, CH$_2$Br); trans-isomer (CDCl$_3$)δ 0.94 (d, CH$_3$CH), 1.06 [s, (CH$_3$)$_3$C], 3.3 (s, OCH$_3$), 3.2–3.7 (m, including ABq for CH$_2$Br).

EXAMPLE 11

1RS,4RS,5SR-4-(5-Benzyloxy-4-methyl-pentyl)-1-methoxy-4-methyl-3,8-dioxabicyclo[3.2.1]octane 7-Benzyloxy-2-[2-bromomethyl-2-methoxy-tetrahydrofuran-5-yl]-6-methyl-heptan-2-ol (17.5 g, 41 mM) is treated with 85% potassium hydroxide (22 g, 335 mM) in distilled dimethylsulfoxide (200 ml) at 65° C. for 1.5 hours. The reaction mixture is allowed to stir at 55° C.

for 18 hours followed by an additional period at 65° C. for 4 hours after which it is poured into cold brine and then partitioned between hexane and brine. The aqueous phase is extracted with hexane and the combined extracts are washed with brine and dried ($Na_2SO_4$). The solvent is removed in vacuo to give the crude product (10.1 g). Purification over silica gel using an ethyl acetate/hexane gradient as the eluent gives 1RS,4RS,5SR-4-(5-benzyloxy-4-methyl-pentyl)-1-methoxy-4-methyl-3,8-dioxabicyclo[3.2.1]octane(2.2 g, 15.5% yield from compound 1):

nmr ($CDCl_3$)δ 0.95 (d, $CH_3CH$), 1.34 (s, $C_4-CH_3$), 3.25 (d, 2H, $-OCH_2CH$), 3.43 (s, 3H, $OCH_3$), 3.83 (AB q, 2H, $C_2-CH_2$), 3.9 (br m, $C_5-H$), 4.50 (s, 2H, $-OCH_2\phi$), 7.37 (s, 5H, aromatic $H$); ms, $M^+348$.

EXAMPLE 12

1RS,4RS,5SR-4-(5-Hydroxy-4-methyl-pentyl)-1-methoxy-4-methyl-3,8-dioxabicyclo[3.2.1]octane Following the procedure for the synthesis of 1RS,4RS,5SR-4-(5-benzyloxy-4-methyl-pentyl)-1-methoxy-4-methyl-3,8-dioxabicyclo[3.2.1]octane, treatment of 7-t-butyldiphenylsiloxy-2-(2-bromomethyl-2-methoxy-tetrahydrofuran-5-yl)-6-methyl-heptan-2-ol (2.3 g) with 85% potassium hydroxide in dimethylsulfoxide gives 1RS,4RS,5SR-4-(5-hydroxy-4-methyl-pentyl)-1-methoxy-4-methyl-3,8-dioxabicyclo[3.2.1]octane.

EXAMPLE 13

1RS,4RS,5SR-4-(5-Hydroxy-4-methyl-pentyl)-1-methoxy-4-methyl-3,8-dioxabicyclo[3.2.1]octane A solution of 1RS,4RS,5SR-4-(5-benzyloxy-4-methyl-pentyl)-1-methoxy-4-methyl-3,8-dioxabicyclo[3.2.1]octane (0.080 g) in 95% ethanol (100 ml) is hydrogenated in the presence of 10% Pd/C (0.025 g) for 90 minutes. The catalyst is removed by filtration through a bed of Celite and washed with ethanol. The combined filtrate is evaporated in vacuo to give 1RS,4RS,5SR-4-(5-hydroxy-4-methyl-pentyl)-1-methoxy-4-methyl-3,8-dioxabicyclo[3.2.1]octane (0.052 g, 88%) as a yellow oil:

nmr ($CDCl_3$)δ 0.92 (d, $CH_3CH$), 1.33 (s, $C_4-CH_3$), 3.2–4.0 (overlapping m, $C_2-CH_2$, $C_5-H$, $-CH_2OH$), 3.4 ($OCH_3$); ms, $M^+258$.

EXAMPLE 14

1RS,4RS,5SR-1-Methoxy-4-methyl-4-(4-methyl-5-oxo-pentyl)-3,8-dioxabicyclo[3.2.1]octane Chromium trioxide (0.77 g) is added to a solution of methylene chloride (100 ml) and pyridine (1.2 g) under nitrogen and the resulting suspension is stirred at room temperature for 1 hour. Celite (5.5 g) is added, the suspension is cooled to -10° C. and 1RS,4RS,5SR-4-(5-hydroxy-4-methyl-pentyl)-1-methoxy-4-methyl-3,8-dioxabicyclo[3.2.1]octane (0.329 g) in methylene chloride (40 ml) is added dropwise. The reaction mixture is stirred for 2 hours and filtered after which the solids are washed with methylene chloride and the filtrate is washed with sodium bicarbonate solution and brine and then dried ($Na_2SO_4$). The solids are filtered and the filtrate is evaporated to give 1RS,4RS,5SR-1-methoxy-4-methyl-4-(4-methyl-5-oxo-pentyl)-3,8-dioxabicyclo[3.2.1]octane (0.325 g, 99%) as an oil:

nmr $CDCl_3$δ 1.20 (d, $CH_3CH$), 1.33 (s, $C_4-CH_3$), 3.2–4.0 (overlapping m, $C_2-CH_2$, $C_5-H$), 3.4 (s, $OCH_3$), 9.2 (d, $-CHO$).

EXAMPLE 15

1RS,4RS,5SR-4-(4,8-Dimethyl-5-hydroxy-8-nonenyl)-1-methoxy-4-methyl-3,8-dioxabicyclo[3.2.1]octane Anhydrous tetrahydrofuran (10 ml) and Mg turnings (0.050 g) are placed in a 25 ml three-necked flask under nitrogen followed by the dropwise addition of 4-bromo-2-methyl-1-butene (0.300 g) in tetrahydrofuran (5 ml). After the Grignard reagent is formed, the reaction is cooled to 0° C. and 1RS,4RS,5SR-1-methoxy-4-methyl-4-(4-methyl-5-oxo-pentyl)-3,8-dioxabicyclo [3.2.1]octane (0.329 g) in tetrahydrofuran (7 ml) is added dropwise and stirred at 0° C. for 0.5 hours. The reaction is warmed to room temperature, stirred an additional 3 hours and then evaporated in vauco. The residue is partitioned between ether and brine, the aqueous phase reextracted with ether (3x) and the combined organic phase washed with brine and dried ($Na_2SO_4$). The solids are filtered and the filtrate evaporated in vacuo to give a yellow oil (0.243 g) which is purified by chromatography on silica (ethyl acetate:hexane gradient) to give 1RS,4RS,5SR-4-(4,8-dimethyl-5-hydroxy-8-nonenyl)-1-methoxy-4-methyl-3,8-dioxabicyclo[3.2.1] octane (0.121 g) as a pale yellow oil: nmr ($CDCl_3$)δ 0.90 (d, $CH_3CH$), 1.33 (s, $C_4-CH_3$), 1.74 (br s, $CH_3C=C$), 3.4 (s, $-OCH_3$), 3.1–4.0 (overlapping M, $C_2-CH_2$, $C_5-H$, $-CHOH$), 4.7 (br s, $C=CH_2$); ms, $M^+325$; trimethylsilyl derivative $M^+398$.

EXAMPLE 16

1RS,4RS,5SR-4-(5-Acetoxy-4,8-dimethyl-8-nonenyl)-1:methoxy-4-methyl-3,8-dioxabicyclo[3.2.1]octane 1RS,4RS,5SR-4-(4,8-dimethyl-5-hydroxy-8-nonenyl)-1-methoxy-4-methyl-3,8-dioxabicyclo[3.2.1]octane (0.120 g) is dissolved in pyridine (1 ml) under nitrogen. Acetic anhydride (0.25 ml) is added and the resulting solution is stirred at room temperature for 2 hours and then at 50° C. for an additional 3 hours. The reaction mixture is cooled, slowly poured into cold sodium bicarbonate solution (10%) and the solution is extracted with ether (4x). The combined ethereal extracts are washed with brine, filtered through phase-separating paper and dried ($Na_2SO_4$). The solids are filtered and the filtrate evaporated in vacuo to give 1RS,4RS,5SR-4-(5-acetoxy-4,8-dimethyl-8-nonenyl)-1-methoxy-4-methyl-3,8-dioxabicyclo[3.2.1]octane as a yellow oil (0.114 g, 85%): nmr ($CDCl_3$)δ 0.90 (d, $CH_3CH$), 1.33 (s, $C_4-CH_3$), 1.74 (br s, $CH_3C=C$), 2.05 (s, $OCOCH_3$), 3.40 (s, $-OCH_3$), 3.1–4.0 (ABq, m, $C_2-CH_2$, $C_5-H$), 4.7–5.0 (overlapping m, $-C=CH_2$ and $CHOAc$).

EXAMPLE 17

1RS,4RS,5SR-4-(5-Acetoxy-4,8-dimethyl-8-nonenyl)-1-hydroxy-4-methyl-3,8-dioxabicyclo[3.2.1]octane 1RS,4RS,5SR-4-(5-Acetoxy-4,8-dimethyl-8-nonenyl)-1-methoxy-4-methyl-3,8-dioxabicyclo[3.2.1]octane (0.110 g) is dissolved in acetone (3 ml), 1 N hydrochloric acid (1 ml) is added and the resulting solution is stirred at 30° C. for 2 hours and then at 55° C. for 3.5 hours. The reaction mixture is then cooled and evaporated in vacuo and the residue is diluted with brine, neutralized to pH 7 with saturated sodium bicarbonate solution and extracted with ethanol (4×50 ml). The combined organic extracts are washed with brine, filtered through phase separatiing paper and dried ($Na_2$-

$SO_4$). The solids are filtered and the filtrate is evaporated in vacuo to give 1RS,4RS,5SR-4-(5-acetoxy-4,8-dimethyl-8-nonenyl)-1-hydroxy-4-methyl-3,8-dioxabicyclo[3.2.1]octane as a yellow oil (0.087 g, 85%):

nmr (CDCl$_3$)δ 0.90 (d, C$\underline{H}_3$CH), 1.33 (s, C$_4$—CH$_3$), 1.74 (br s, C$\underline{H}_3$C=C), 2.05 (s, C$\underline{H}_3$CO$_2$—), 3.3–4.1 (overlapping m, C$_2$-CH$_2$, C$_5$—$\underline{H}$, OH), 4.7–5.0 (overlapping m, —C=C$\underline{H}_2$ and —C$\underline{H}$OAc).

EXAMPLE 18

1RS,4SR,5RS-4-(5-Acetoxy-4,8-dimethyl-8-nonenyl)-4-methyl-3,8-dioxabicyclo[3.2.1]octane-1-acetic acid, ethyl ester Carbethoxymethylene-triphenylphosphorane (0.165 g) and 1RS,4SR,5RS-4-(5-acetoxy-4,8-dimethyl-8-nonenyl)-1-hydroxy-4-methyl-3,8-dioxabicyclo[3.2.1]octane (0.081 g) are mixed neat and heated to 120° C. for 18 hours. The resulting solution is cooled and purified over silica gel (ethyl acetate/hexane gradients) to give 1RS,4SR,5RS-4-(5-acetoxy-4,8-dimethyl-8-nonenyl)-4-methyl-3,8-dioxabicyclo[3.2.1]octane-1-acetic acid, ethyl ester as a yellow oil (0.048 g, 50%):

nmr (CDCl$_3$)δ 0.94 (d, C$\underline{H}_3$CH), 1.27 (t, OCH$_2$C$\underline{H}_3$), 1.33 (s, C$_4$—CH$_3$), 1.73 (s, C$_8$—CH$_3$), 2.05 (s, OCOC$\underline{H}_3$), 2.6 (s, C$_1$—C$\underline{H}_2$CO$_2$Et), 3.4–4.0 (overlapping m, C$_2$—C$\underline{H}_2$ and C$_5$—$\underline{H}$), 4.18 (q, OC$\underline{H}_2$CH$_3$), 4.7–5.0 (br s and m, C=C$\underline{H}_2$ and C$\underline{H}$OAc); ms, m/e 364 (M—HOAc), 337 (M—CH$_2$CO$_2$Et).

EXAMPLE 19

1RS,4SR,5RS-4-(5-Acetoxy-4,8-dimethyl-7-nonenyl)-4-methyl-3,8-dioxabicyclo[3.2.1]octane-1-acetic acid, ethyl ester 1RS,4SR,5RS-4-(5-Acetoxy-4,8-dimethyl-8-nonenyl)-4-methyl-3,8-dioxabicyclo[3.2.1]octane-1-acetic acid, ethyl ester (0.030 g) in benzene (1 ml) is added to a solution of p-toluenesulfonic acid-monohydrate (6 mg) in benzene (7 ml) and the resulting clear solution is heated at reflux with a Dean-Stark trap to remove water for 44 hours. The reaction mixture is cooled, diluted with ether (75 ml) and washed with dilute sodium bicarbonate and brine. The organic phase is filtered through phase separating paper and dried (Na$_2$SO$_4$). Filtration of the solids and evaporation in vacuo gives 1RS,4SR,5RS-4-(5-acetoxy-4,8-dimethyl-7-nonenyl)-4-methyl-3,8-dioxabicyclo[3.2.1]octane-1-acetic acid, ethyl ester as a colorless oil (0.029 g, 97%): nmr (benzene d$_6$) δ 0.7 (overlapping d and t, C$\underline{H}_3$CH and C$\underline{H}_3$CH$_2$), 1.37 [2s, (CH$_3$)$_2$C=], 1.55 (s, OCOC$\underline{H}_3$), 2.23 (s, C$_1$—C$\underline{H}_2$CO$_2$Et), 3.2–4.0 (overlapping m, —OC$\underline{H}_2$CH$_3$, C$_2$—C$\underline{H}_2$, C$_5$—$\underline{H}$), 4.6–5.2 (overlapping m, >C=C$\underline{H}$, —C$\underline{H}$OAc).

EXAMPLE 20

1RS,4SR,5RS-4-(4,8-Dimethyl-5-hydroxy-7-nonen-1-yl)-4-methyl-3,8-dioxabicyclo[3.2.1]octane-1-acetic acid (I)

1RS,4SR,5RS-4-(5-Acetoxy-4,8-dimethyl-7-nonenyl)-4-methyl-3,8-dioxabicyclo[3.2.1]octane-1-acetic acid, ethyl ester (0.029 g) is dissolved in methanol (2 ml) and 2.0 N sodium hydroxide (2 ml) is added to give a cloudy suspension. A clear solution results after 0.25 hours and it is stirred at room temperature for an additonal 3.5 hours. The methanol is evaporated in vacuo and the residue is partitioned between brine and ether. The aqueous layer is acidified to pH 3 with 10% hydrochloric acid and extracted with ether. The ether extracts are combined, washed with brine and dried (Na$_2$SO$_4$). Evaporation of the solvent in vacuo gives 1RS,4SR,5RS-4-(4,8-dimethyl-5-hydroxy-7-nonen-1-yl)-4-methyl-3,8-dioxabicyclo[3.2.1]octane-1-acetic acid as a colorless oil (0.023 g, 96%):

nmr (CDCl$_3$)δ 0.88 (d, C$\underline{H}_3$CH), 1.31 (s, C$_4$—CH$_3$), 1.63 and 1.71 [br s, (C$\underline{H}_3$)$_2$C=C], 2.60 (s, —C$\underline{H}_2$CO$_2$H), 3.4–4.0 (overlapping m, C$_2$—CH$_2$, C$_5$—$\underline{H}$ and —C$\underline{H}$OH), 4.9–5.2 [m, (CH$_3$)$_2$C—C=C$\underline{H}$—]: ir (neat) μ: 2.90 (OH), 5.8 (C=O); ms, M$^+$ 498, bis-trimethylsilyl derivative.

PREPARATION OF STARTING MATERIAL

EXAMPLE A

1-Benzyloxy-2-methyl-6-oxo-heptane

A. 6,6-Ethylenedioxy-2-methyl-heptanol (187.1 g, 0.995 M) in benzene (1.5 l) is added to a slurry of sodium hydride (50% benzene washed, 71.7 g, 1.49 M) in benzene (4 l) and the mixture is allowed to stir for 5 hours at room temperature. Benzyl bromide (147.3 ml, 1.24 M) in benzene is added and the reaction is allowed to stir at reflux for 16 hours. The solvent is removed in vacuo and the residue obtained is poured into ice water and partitioned between ether and brine. The aqueous phase is extracted with ether and the combined extracts washed with brine and dried (Na$_2$SO$_4$). The solvent is removed in vacuo to give the desired benzyl-ketal which is used as is in the next step.

B. The benzyl-ketal (277 g, 1 M) in acetone (4.25 l) is treated with 10% hydrochloric acid (400 ml) and the mixture is allowed to stir at room temperature for 3 hours. The reaction mixture is neutralized with sodium bicarbonate, filtered to remove the salt and the solvent is removed in vacuo. The residue is partitioned between ether and water, the aqueous phase is extracted with ether and the combined ether extracts are washed with brine and dried (Na$_2$SO$_4$). The solvent is removed to give the crude product (248 g). Purification via silica chromatography using an ethyl acetate/hexane gradient as the eluent gives 1-benzyloxy-2-methyl-6-oxo-heptane (162 g, 70%):

nmr (CDCl$_3$)δ 0.95 (d, 3H, C$\underline{H}_3$CH), 2.13 (s, 3H, C$\underline{H}_3$CO), 2.42 (br t, 2H, COC$\underline{H}_2$), 3.3 (d, 2H, —CHC$\underline{H}_2$O), 4.54 (s, 2H, OC$\underline{H}_2$), 7.37 (s, 5H, aromatic H).

EXAMPLE B 8-t-Butyldiphenylsiloxy-3,7-dimethyl-1-octen-3-ol 1-t-Butyldiphenylsiloxy-2-methyl-6-oxo-heptane (58.5 g) is added in anhydrous tetrahydrofuran (500 ml) to vinyl magnesium bromide (1.5 M, 166 ml) at 0° C. and the mixture is allowed to stir overnight at room temperature. A saturated aqueous solution of ammonium chloride (750 ml) is added slowly to the chilled reaction mixture. The mixture is then acidified to pH 6 with 10% hydrochloric acid. The organic layer is separated and the aqueous phase is extracted with ether (2×). The combined organic phases are washed with brine and dried (Na$_2$SO$_4$). The solvent is removed in vacuo to give the crude product (64.85 g, 100% as a yellow oil of suitable purity for the following step. A 4 g portion is purified via silica gel chromatography using ethyl acetate-hexane gradients to give 8-t-butyldiphenylsiloxy-3,7-dimethyl-1-octen-3-ol (2.8 g):

ir (neat) 2.94μ (OH); nmr (CDCl$_3$)δ 0.90 (d, C$\underline{H}_3$CH<), 1.05 (C$\underline{H}_3$)$_3$C),

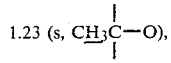

1.23 (s, CH₃C—O), 3.45 (d, 2H OCH₂CH), 4.87–6.17 (ABX m, 3H, CH═CH₂), 7.23–7.8 (m, 10H, 2φ); ms no m/e 410 (parent peak) but m/e 353 (M-57), 335 (353-18).

EXAMPLE C

8-Benzyloxy-3,7-dimethyl-1-octen-3-ol

Following the procedure for the synthesis of 8-t-butyldiphenylsiloxy-3,7-dimethyl-1-octen-3-ol, treatment of 1-benzyloxy-2-methyl-6-oxo-heptane (1.55 g) after silica gel chromatography with an ethyl acetate-hexane gradient as the eluent gives 8-benzyloxy-3,7-dimethyl-1-octen-3-ol (0.605 g) as a yellow oil:

nmr (CDCl₃)δ0.93 (d, CH₃CH), 1.27 (s, C₃—CH₃), 3.3 (d, OCH₂CH), 4.5 (s, OCH₂Ph), 4.8–6.2 (m, vinyl H), 7.33 (s, aromatic H).

EXAMPLE D

1-Benzyloxy-2,6-dimethyl-10-oxo-undec-6-ene

A. Ethyl acetoacetate (81.8 g, 0.62 M) is treated with sodium ethoxide prepared by the addition of sodium (14.18 g, 0.62 M) to absolute ethanol (400 ml) with cooling. After stirring at room temperature for 1 hour the reaction mixture is cooled to 0° C. and 8-benzyloxy-3,7-dimethyl-2-octenyl chloride (18.9 g, 67.5 mM) is added. After 1.5 hours at 0° C. the reaction mixture is stirred at room temperature for 2 hours. The solvent is removed in vacuo, the residue poured into ice water, neutralized with 1 N hydrochloric acid and partitioned between ether and brine. The aqueous phase is extracted with ether and the combined extracts are washed with brine and dried (Na₂SO₄). The solvent is removed in vacuo to give the crude β-ketoester which is used as is in the next step.

B. The β-ketoester derived from 8-benzyloxy-3,7-dimethyl-2-octenyl chloride (25.2 g, 67.5 mM) is treated with 2 N sodium hydroxide/methanol (675 ml) and after 10 minutes water (675 ml) is added. The reaction mixture is heated at reflux for 3 hours. The solvent is removed in vacuo and the residue obtained is treated with ether and brine. The layers are separated, the aqueous phase is extracted with ether, and the combined extracts are washed with brine and dried (Na₂SO₄). The solvent is removed in vacuo to give the crude product (16 g). Purification over silica gel using 5% ethyl acetate/hexane as the eluent gives 1-benzyloxy-2,6-dimethyl-10-oxo-undec-6-ene (12.4 g, 61%) with a 83/17 E/Z isomer ratio by gas chromatography:

nmr (CDCl₃)δ 0.93 (d, CH₃CH), 1.63 (br s, E—CH₃C═C), 1.68 (br s, Z—CH₃C═C), 2.1 (s, 3H, Ch₃CO), 3.27 (d, —O—CH₂CH), 4.49 (s, 2H, —OCH₂φ), 5.05 (br m, 1H, C═CH), 7.34 (s, 5H, aromatic H).

EXAMPLE E

6 E/Z-t-Butyldiphenylsiloxy-2,6-dimethyl-10-oxo-undec-6-ene

· 8-t-Butyldiphenylsiloxy-3,7-dimethyl-1-octen-3-ol (60.33 g) is treated with ethyl acetoacetate (28.8 ml) and anhydrous sodium acetate (232 mg) and the mixture is allowed to stir for 2 hours at 205° C. under a short path distillation head to remove the ethanol formed in the reaction. The crude reaction mixture is purified via silica gel chromatography using ethyl acetate-hexane gradients to give 6 E/Z-1-t-butyldiphenylsiloxy-2,6-dimethyl-10-oxo-undec-6 -ene (32.9 g, 50%) as a yellow oil: ir (neat) 5.8μ (C═O); nmr (CDCl₃)δ0.9 (d, CH₃CH<), 1.05 [s, (CH₃)₃C],

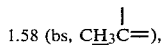

1.58 (bs, CH₃C═), 2.08

(s, CH₃C═O), 3.48 (d, 2H, OCH₂CH<), 5.03 (b, 1H, C═CH—), 7.17–7.8 (m, 10 H, 2φ); m.s., M+450 (parent peak) not observed but M-57 (t-Bu) 393 present. A mixture of 60/40 E/Z isomers is observed by gas chromatography.

EXAMPLE F 8-t-Butyldiphenylsiloxy-1-bromo-3,7-dimethyl-oct-2-ene

A. A solution of 2.25 N hydrogen bromide in ether (1.8 ml) is added to 8-t-butyldiphenylsiloxy-3,7-dimethyl-1-octen-3-ol (1.64 g) in ether (15 ml) dropwise at −70° C. The solution is warmed at 0° C. for 2 hours followed by the addition of solid sodium bicarbonate and then aqueous sodium bicarbonate to pH 7. The layers are separated, the aqueous layer re-extracted with ether and the combined ether extracts are washed with aqueous sodium bicarbonate, brine and dried (Na₂SO₄). The solids are filtered and the filtrate is evaporated in vacuo to give 8-t-butyldiphenylsiloxy-1-bromo-3,7-dimethyl-oct-2-ene as a yellow oil (1.66 g).

B. Sodium (552 mg) is added to ethanol (absolute, 10 ml) and after formation of sodium ethoxide, the solution is cooled and ethyl acetoacetate (3.12 g) is added and stirred for 1 hour, the ethanol is evaporated in vacuo, tetrahydrofuran (15 ml) is added to the sodium salt and the mixture cooled to 0° C. 8t-Butyldiphenyl-siloxy-1-bromo-3,7-dimethyl-oct-2-ene in tetrahydrofuran (5 ml) is added dropwise and the resulting suspension is stirred for 16 hours at room temperature. The solvent is evaporated in vacuo and the residue partitioned between ether and dilute hydrochloric acid. The organic layer is dried (Na₂SO₄) and filtered, the filtrate evaporated in vacuo to give the β-keto ester (1.7 g):

nmr (CDCl₃)δ 0.94 (d, CH₃CH), 1.08 [s, (CH₃)₃C—], 1.27 (t, CH₃CH₂), 1.63 (s, CH₃—C═), 2.2 (s, CH₃CO —), 2.56

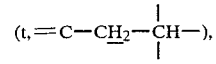

(t, ═C—CH₂—CH—), 3.4 (overlapping d and m, —HCCH₂—O— and —CH₂CH), 4.19 (q, —OCH₂CH₃), 5.04 (br t, —C═CH), 7.2–7.8 (aromatic H); GC, E:Z ratio of 7:3.

The β-keto ester (0.50 g) is added to a solution containing methanolic 2 N sodium hydroxide (5 ml) and water (5 ml) and the mixture is heated to reflux for 1½ hours. The solvent is removed in vacuo and the residue is partitioned between ether and brine. The organic layer is dried (Na₂SO₄) and filtered, the filtrate is evaporated in vacuo to give 6 E/Z-1-t-butyldiphenylsiloxy-2,6-dimethyl-10-oxo-undec-6-ene (0.428 g, 99%) as a yellow oil: nmr (CDCl₃) and ms, as for 6 E/Z-1-t-butyldiphenylsiloxy-2,6-dimethyl-10-oxo-undec-6-ene synthesized by Example E; GC indicates a 7:3 ratio of E:Z isomers.

EXAMPLE G

8-Benzyloxy-1-bromo-3,7-dimethyl-oct-2-ene

Following the procedure for the synthesis of 8-t-butyldiphenylsiloxy-1-bromo-3,7-dimethyl-oct-2-ene, treatment of 8-benzyloxy-3,7-dimethyl-1-octen-3-ol (0.605 g) gives 8-benzyloxy-1-bromo-3,7-dimethyl-oct-2-ene (0.675 mg, 90% yield, 7:3 E:Z).

The corresponding β-keto ester is formed from 8-benzyloxy-1-bromo-3,7-dimethyl-oct-2-ene (0.673 g) on treatment with sodioethyl acetoacetate in tetrahydrofuran and is converted to 1-benzyloxy-2,6-dimethyl-10-oxo-undec-6-ene (0.365 g) upon base treatment as above; GC 7:3 ratio E:Z.

EXAMPLE H

Ethyl-8-benzyloxy-3,7-dimethyl-2-octenoate

Distilled triethylphosphonoacetate (241 g, 1.08 M) in benzene (1 l) is added to a slurry of 99% sodium hydride (22.8 g, 0.95 M) in benzene (2 l). The mixture is heated at 70° C. for 3 hours. 1-Benzyloxy-2-methyl-6-oxo-heptane (88.7 g, 0.38 M) in benzene (0.5 l) is added and the temperature is maintained at 70° C. for 2 hours. The reaction mixture is cooled to room temperature, brine is added and the suspension is neutralized with 10% hydrochloric acid and partitioned between ether and brine. The aqueous phase is extracted with ether and the combined extract is washed with brine and dried (Na₂SO₄). The solvent is removed in vacuo to give ethyl-8-benzyloxy-3,7-dimethyl-2-octenoate (186 g). Purification via silica gel chromatography using an ethyl acetate/hexane gradient as the eluent gives ethyl-8-benzyloxy-3,7-dimethyl-2-octenoate (94.6 g, 82%, a mixture of 80/20 E/Z isomers by NMR analysis):
nmr (CDCl₃)δ 0.95 (d, 3H, C$\underline{H}_3$CH), 1.3 (t, 3H, C$\underline{H}_3$CH₂), 1.88 (d, Z—C=C—C$\underline{H}_3$), 2.17 (d, E—C=C—C$\underline{H}_3$), 3.32 (d, 2H CHC$\underline{H}_2$—O—), 4.18 (q, 2H, OC$\underline{H}_2$CH₃), 4.53 (s, 2H, OC$\underline{H}_2$Ph), 5.66 (m, 1H, C=C$\underline{H}$), 7.37 (s, 5H, aromatic $\underline{H}$).

EXAMPLE I

8-Benzyloxy-3,7-dimethyl-2-octenol

Ethyl-8-benzyloxy-3,7-dimethyl-2-octenoate (94.6 g, 0.31 M) in ether (1.4 l) is added to a slurry of lithium aluminum hydride (47.3 g, 1.25 M) in ether (3.3 l) at 0° C. and the reaction mixture is allowed to stir at 0° C. for 4 hours. Wet ether (750 ml) is added slowly and the mixture is acidified with 1N hydrochloric acid. The organic phase is separated, the aqueous phase is extracted with ether and the combined organic extracts are washed with brine and dried (Na₂SO₄). The solvent is removed in vacuo to give the crude product (77.6 g, 95%). Purification over silica gel using an ethyl acetate/hexane gradient as the eluent gives fractions of varying mixtures of isomers. A collection of fractions that gives 17.7 g of 8-benzyloxy-3,7-dimethyl-2-octenol with an 85/15 E/Z isomer ratio by gas chromatography analysis is used in the next step:
nmr (CDCl₃)δ 0.94 (d, 3H, C$\underline{H}_3$CH), 1.67 [br s (E) C$\underline{H}_3$C=C], 1.73 [br s, (Z) CH₃C=C], 2.02 (br m, C=C—C$\underline{H}_2$C), 3.3 (d, 2H —CHC$\underline{H}_2$O—), 4.13 (d, 2H, =CH—C$\underline{H}_2$OH), 4.50 (s, 2H, —OC$\underline{H}_2$φ), 5.30 (br t, 1H, C=C$\underline{H}$), 7.33 (s, 5H, aromatic $\underline{H}$).

EXAMPLE J

8-Benzyloxy-3,7-dimethyl-2-octenyl chloride

8-Benzyloxy-3,7-dimethyl-2-octenol (17.7 g, 67.6 mM) in collidine (13.35 ml, 101 mM) is treated with lithium chloride (2.88 g, 67.9 mM) in dimethylformamide (145 mg). The reaction mixture is cooled to 0° C. and methane-sulfonyl chloride (7.6 ml, 98.2 mM) is added neat. The thick suspension is allowed to stir at 0° C. for 0.75 hours and then at room temperature for 2 hours.

The reaction mixture is poured into ice water, extracted with hexane and the combined extracts are washed with a saturated copper sulfate solution and brine and then dried (Na₂SO₄). The solvent is removed in vacuo to give 8-benzyloxy-3,7-dimethyl-2-octenyl chloride (19.7 g).

EXAMPLE K

6,6-Ethylenedioxy-2-methyl-hept-1-ene

To a slurry of methyl triphenylphosphonium bromide (218 g) in anhydrous tetrahydrofuran (1.8 l) cooled to 0° C. is added 1.6 M n-butyllithium (270 ml) and 2.6 M n-butyllithium (37.5 ml). After stirring for 1 hour, 6,6-ethylenedioxy-heptane-2-one (91.3 g) in anhydrous tetrahydrofuran (200 ml) is added dropwise and the mixture stirred for 1.5 hours at room temperature. The reaction mixture is then filtered and the filter cake washed with ether. The solvent is removed via distillation at atmospheric pressure. The crude residue is purified via vacuum distillation to give 6,6-ethylenedioxy-2-methyl-hept-1-ene (33.95 g, 38%) bp 75°@15 mm:
nmr (CDCl₃)δ 1.32

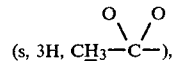

(s, 3H, C$\underline{H}_3$—C—), 1.7 (s, 3H, C$\underline{H}_3$—C=). 3.92 (s, 4H, OC$\underline{H}_2$CH₂O), 4.67 (bs, 2H, >C=C$\underline{H}_2$).

EXAMPLE L

2-Methyl-6-oxo-hept-1-ene

A solution of 6,6-ethylenedioxy-2-methyl-hept-1-ene (12.2 g) in acetone (300 ml) and 10% hydrochloric acid (12 ml) is stirred at room temperature for 1.5 hours. The reaction is neutralized to pH 7 with a sodium bicarbonate solution and the resulting solids are filtered. The acetone is removed in vacuo and the residue is partitioned between ether and brine. The ether extract is dried (Na₂SO₄) and evaporated in vacuo to give 2-methyl-6-oxo-hept-1-ene as a pale yellow liquid (6.4 g):
nmr (CDCl₃,δ) 1.7 (br s, C$\underline{H}_3$—C=), 2.12 (s, C$\underline{H}_3$C=O), 2.4 (t, J=6 Hz, C$\underline{H}_2$C=O), 4.69 (br s, 2H, $\underline{H}_2$C=C).

EXAMPLE M

6,6-Ethylenedioxy-2-methyl-heptanol

To a solution of 6,6-ethylenedioxy-2-methyl-hept-1-ene (33.95 g) in hexane (132 ml) under a nitrogen atmosphere is added borane-methyl sulfide complex (7.05 ml) at 0° C. over a half hour period. The reaction is allowed to stir for 3 hours at room temperature and is treated with 95% ethanol (68 ml) and 3N sodium hydroxide (21.8 ml), cooled to 0° C., followed by the dropwise addition of 30% hydrogen peroxide (24.5 ml) to maintain a temperature of 25°-35° C. The reaction mixture is heated at reflux for one half hour, poured into ice water (500 ml) and partitioned between ether and water. The aqueous phase is extracted with ether and the combined extracts are washed with brine and dried (Na₂SO₄). The solvent is removed in vacuo to give 6,6-ethylenedioxy-2-methyl-heptanol (33.35 g, 89%): nmr (CDCl₃,δ), 0.93 (d, 3H, C$\underline{H}$₃CH<), 1.32

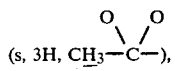
(s, 3H, C$\underline{H}$₃—C—), 3.45 (bd, 2H, CHC$\underline{H}$₂O), 3.93 (s, 5H, OC$\underline{H}$₂C$\underline{H}$₂O and CH₃C$\underline{H}$<).

EXAMPLE N 1-t-Butyldiphenylsiloxy-6,6-ethylenedioxy-2-methyl-heptane

Imidazole (26.5 g) is added to a solution of 6,6-ethylenedioxy-2-methyl-heptanol (33.35 g) in dimethylformamide (50 ml). A solution of t-butyldiphenylsilyl chloride (52.2 g) in dimethylformamide (200 ml) is added dropwise to the reaction mixture and allowed to stir for 3 hours at room temperature. The reaction mixture is extracted with hexane (3×300 ml) and the combined extract is washed with brine and dried (Na₂SO₄). The solvent is removed in vacuo to give 1-t-butyldiphenylsiloxy-6,6-ethylenedioxy-2-methyl-heptane (75.35 g, 99.6%): nmr (CDCl₃δ), 0.91 (d, 3H, C$\underline{H}$₃CH), 1.03 [s, (C$\underline{H}$₃)₃C],

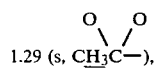
1.29 (s, C$\underline{H}$₃C—), 3.47 (d, CHC$\underline{H}$₂O), 3.88 (s, OC$\underline{H}$₂C$\underline{H}$₂O), 7.2-7.8 (m, 10H, 2φ).

EXAMPLE O 1-t-Butyldiphenylsiloxy-2-methyl-6-oxo-heptane 1-t-Butyldiphenylsiloxy-6,6-ethylenedioxy-2-methyl-heptane (75.35 g) in acetone (2 l) is treated with 10% hydrochloric acid (75 ml) and the solution is allowed to stir at room temperature for 2½ hours. The reaction mixture is neutralized with a saturated sodium bicarbonate solution (150 ml), the salt is removed by filtration and the solvent is removed in vacuo. The resulting residue is partitioned between ether and water, the aqueous phase is extracted with ether, and the combined ether extracts are washed with brine and dried (Na₂SO₄). The solvent is removed in vacuo to give the crude product which is purified via silica gel chromatography (5% EtOAc/hexane) to give 1-t-butyldiphenylsiloxy-2-methyl-6-oxo-heptane (61.95 g, 92%); ir (neat) 5.85 μ (C=O); nmr (CDCl₃,δ), 0.92 (d, 3H, C$\underline{H}$₃CH<), 1.05 [s, (C$\underline{H}$₃)₃], 2.07 (s, 3H, C$\underline{H}$₃C=O), 3.45 (d, 2H, CHC$\underline{H}$₂O), 7.2-7.8 (m, 10H, 2φ).

We claim:

1. The process for the preparation of a compound of the formula

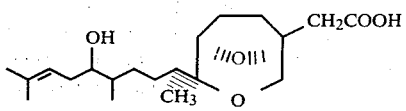

which comprises reacting a compound of the formula

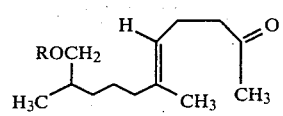

with lithium diisopropylamide followed by reaction with trimethylsilyl chloride in the presence of a base to form a compound of the formula

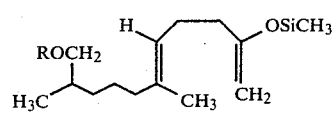

reacting the product formed with a brominating agent to form a compound of the formula

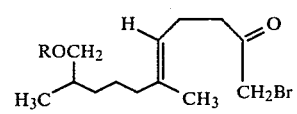

reacting the brominated product with a peracid to form a compound of the formula

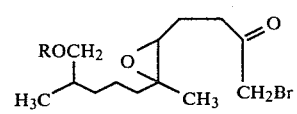

reacting the epoxide formed with acid to form a 5-membered ring hemiketal of the formula

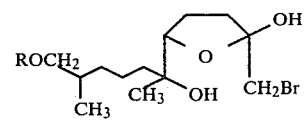

reacting the hemiketal with an alkylating agent to form a bromohydroxy acetal of the formula

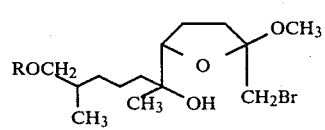

cyclizing the bromo tertiary alcohol to form a bicyclic oxido-oxepane of the formula

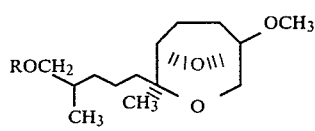

oxidizing the alcohol with an oxidizing agent to form an aldehyde of the formula

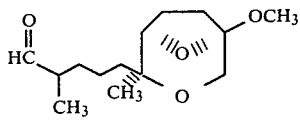

reacting the aldehyde with a Grignard reagent of the formula

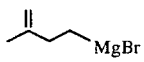

to form a compound of the formula

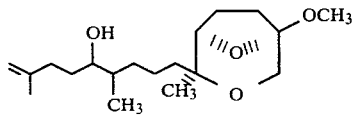

esterifying the alcohol formed with an esterifying agent to form an ester of the formula

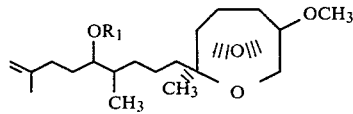

hydrolyzing the ketal with a hydrolyzing agent to form a hemiketal of the formula

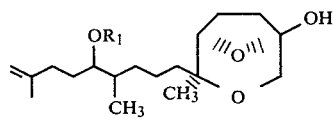

reacting the hemiketal formed with a compound of the formula

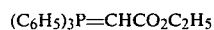

to form a compound of the formula

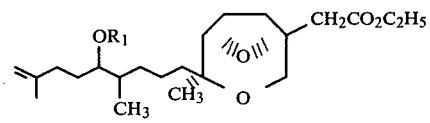

reacting the product formed with an isomerizing agent to form a compound of the formula

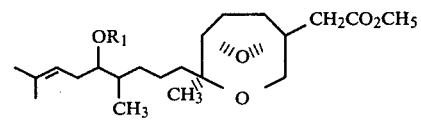

and reacting the product formed with an aqueous alcoholic base, wherein R is a benzyl or a t-butyldiphenylsilyl group and $R_1$ is lower alkanoyl.

2. The process of claim 1 wherein R is benzyl.

3. The process of claim 1 wherein R is t-butyldiphenylsilyl.

4. The process of claim 1 wherein the initial base is sodium bicarbonate.

5. The process of claim 1 wherein the peracid is m-chloroperbenzoic acid.

6. The process of claim 1 wherein the brominating agent is N-bromosuccinimide.

7. The process of claim 1 wherein the acid is hydrochloric acid.

8. The process of claim 1 wherein the alkylating agent is trimethylorthoformate.

9. The process of claim 1 wherein the oxidizing agent is chromium trioxide-pyridine.

10. The process of claim 1 wherein the esterifying agent is acetic anhydride.

11. The process of claim 1 wherein the hydrolyzing agent is hydrochloric acid.

12. A compound of the formula

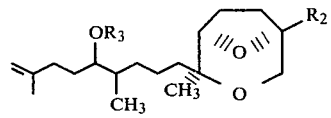

wherein $R_3$ is hydrogen or lower alkanoyl and $R_2$ is hydroxy, methoxy or carboethoxymethylene.

13. A compound of the formula

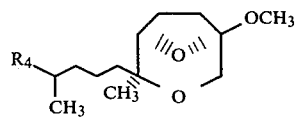

wherein $R_4$ is $CH_2OH$, $CHO$ or $C_6H_5CH_2OCH_2$.

14. A compound of the formula

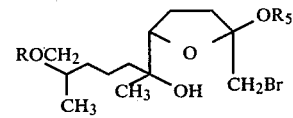

wherein R is benzyl or t-butyldiphenylsilyl and $R_5$ is hydrogen or methyl.

* * * * *